United States Patent
Bhatt et al.

[11] Patent Number: 6,106,809
[45] Date of Patent: *Aug. 22, 2000

[54] HAIR SPRAY COMPOSITIONS CONTAINING CARBOXYLATED POLYURETHANE RESINS

[75] Inventors: Darshna Bhatt, Schaumburg; Ramiro Galleguillos, Glendale Heights, both of Ill.

[73] Assignee: Helene Curtis, Inc., Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/717,113

[22] Filed: Sep. 20, 1996

[51] Int. Cl.$^7$ .......................................................... A61K 9/12
[52] U.S. Cl. ........................... 424/45; 424/47; 424/70.1; 424/70.11
[58] Field of Search ...................... 424/45, 47, DIG. 1, 424/DIG. 2, 70.11, 78.17, 78.37

[56] References Cited

U.S. PATENT DOCUMENTS

| | | |
|---|---|---|
| 3,975,350 | 8/1976 | Hudgin et al. . |
| 4,156,066 | 5/1979 | Gould . |
| 4,359,558 | 11/1982 | Gould et al. . |
| 4,408,023 | 10/1983 | Gould et al. . |
| 4,424,305 | 1/1984 | Gould et al. . |
| 4,439,583 | 3/1984 | Gould et al. . |
| 4,439,585 | 3/1984 | Gould et al. . |
| 4,445,521 | 5/1984 | Grollier et al. . |
| 4,496,535 | 1/1985 | Gould et al. . |
| 4,729,914 | 3/1988 | Kliment et al. . |
| 4,743,673 | 5/1988 | Johnston et al. . |
| 4,780,512 | 10/1988 | Gould et al. . |
| 5,120,816 | 6/1992 | Gould et al. . |
| 5,164,177 | 11/1992 | Bhatt et al. . |
| 5,334,691 | 8/1994 | Gould et al. . |
| 5,639,448 | 6/1997 | Galleguillos . |

FOREIGN PATENT DOCUMENTS

| | | |
|---|---|---|
| 0 619 111 | 10/1994 | European Pat. Off. . |
| 94/03510 | 2/1994 | WIPO . |

*Primary Examiner*—Thurman K. Page
*Assistant Examiner*—R. Bhwa
*Attorney, Agent, or Firm*—Mathew Boxer

[57] ABSTRACT

A hair spray composition comprising:
(a) about 0.25% to about 6% by weight of a carboxylated polyurethane resin;
(b) about 0.25% to about 6% by weight of a second hair fixative resin;
(c) about 0% to about 80% by weight of an alcohol; and
(d) about 15% to about 95% by weight water,
wherein the carboxylated polyurethane resin has a weight average molecular weight of about 10,000 to about 80,000.

1 Claim, 1 Drawing Sheet

FIG. 1

HAIR SPRAY COMPOSITIONS CONTAINING CARBOXYLATED POLYURETHANE RESINS

FIELD OF INVENTION

The present invention is directed to hair spray compositions that are applied to the hair to maintain the hair in a predetermined shape or configuration. The compositions impart excellent hair set retention, feel, and washability to sprayed hair. In particular, the present invention relates to aerosol and nonaerosol hair spray compositions comprising a carboxylated polyurethane resin, a second hair fixative resin, an organic solvent, and water.

BACKGROUND OF THE INVENTION

Normal hair can be so fine, limp, and lacking in body that the hair does not hold a hair set well. Furthermore, the hair can further lose body and be weakened as a result of being subjected to chemically active hair treatments, such as permanent waves and tints. Additionally, hair can be weakened even further by other contributing factors, such as bleaching by the sun or chlorinated swimming pool water.

Hair setting is basically the process of shaping wet hair by the steps of stretching the hair by curling the hair, fixing the hair in place by drying, then combing to give the finishing touches to provide the desired hairstyle. In particular, the setting of wet hair can be accomplished by making flat curls from strands of hair and fixing the curls with hairpins to produce "pin curls." Similarly, wet hair can be set by using any of a variety of rollers or curlers to mechanically fix the hair. In either case, winding of the wet hair is followed by drying, either ambient air drying, electric drying, or hot air, i.e., blow, drying.

The inherent problem encountered in hair setting is the natural tendency of hair to return to its natural shape. For example, set hair returns to its natural shape almost immediately if moistened. Likewise, high humidity conditions accelerate the tendency of hair to return to its natural shape. Therefore, intensive efforts have been directed toward providing a hair set with sufficient holding power to maintain the designed hairstyle until at least the next shampoo, and, therefore, giving the hair set a degree of permanency.

As indicated by the natural tendency of hair to return to its natural shape, hair is an elastic structure. As a result, slight deformations in the hair structure resulting from setting the hair are completely reversible. However, the rate of return of the hair to its natural shape is dependant upon the method used to deform, or set, the hair. Hair sets performed with wet strands of hair being rolled tightly, either in curls around the finger or on curlers, followed by drying the hair and unrolling the curlers after drying, corresponds to the release of hair from a deformation-causing load. The deformation, or set, obtained can last for several days, but the set will not be retained if the hair is wetted.

Investigators have sought to delay the combined action of natural forces and moisture that cause hair to return to its original state by applying solutions containing naturally occurring or synthetic polymers after the hair is shaped into a desired configuration. When applied to shaped hair from aqueous or aqueous/alcoholic solutions, and after drying, the polymers leave a film on the hair to help maintain the hair in the previously shaped configuration. The polymeric film promotes cohesion and gives stability to the hair set to maintain the hold of the hair set. The principal objective of a setting lotion is to cover the previously styled hair with an invisible polymeric film that gives the styled hair a degree of rigidity and protects the hairstyle against wind and humidity.

Hair spray products act in a similar manner. The hair spray products are applied to wet and/or dry hair and contain a polymer that remains fixed on the previously styled hair and effects the hair in various ways. For example, a "mechanical" effect is exerted on each individual hair. The film-forming polymers are used to provide a flexible sheath of polymeric film on the shaped hair after drying, and, therefore, for mechanical reasons, retard the return of each individual hair to its natural shape. In addition, the polymeric film provides an overall stiffening of the hair. The hair behaves as if the individual hair strands are welded together, and the final hairstyle has better cohesion, therefore, resisting the natural forces that return the hair to its natural shape. Finally, the polymeric film protects the hair from humidity. The ability of the polymeric film to attract and absorb water preferably is minimal, such that the polymeric film retards moisture uptake by hair and retards the return of the hair to its natural state.

The general principles of hair setting are thoroughly discussed by C. Zviak, in *The Science of Hair Care,* Marcel Dekker, pp. 149–181 (1986). Zviak reviews both the polymers used in hair setting products and the formulation principles used to produce a hair set product that provides such beneficial hair set properties as improved hairstyle hold, easy application and combing, quick drying and nonstickiness, good hair body and bounce, increased hair volume and gloss, and hydrophobicity. It is evident that in the formulation of any end-use hairstyling product, some of these benefits must be sacrificed to some degree to achieve a competing benefit. In developing a hair set product, it is important that the hair retains its preset configuration, feels like natural hair, and does not generate excessive crust or flaking. Therefore, the formulation of consumer-acceptable hair set products has proved difficult.

To overcome some of the inherent disadvantages of the polymers utilized to set the hair, hair set products are made available in diversified forms in an attempt to minimize the drawbacks of the particular polymer used in the formulation. For example, hair set products are available as plasticizing lotions, plasticizing gels, aerosol foams, all-purpose lotions, hair sprays, holding lotions, conditioners, and shampoos. Prior investigators also have used a blend of polymers in order to improve hair set properties. To date, the ideal hair set composition has not been developed.

Nonionic, cationic, and anionic polymers have been used in hair set products, with the anionic polymers providing the best hair set results. However, anionic polymers also have disadvantages, such as high water solubility, and, therefore, low hydrophobicity. Anionic surfactants also have a low substantivity on hair fibers, and, therefore, generate a crust and flakes due to easy elimination from the hair by combing and brushing. As a result, investigators have continued to search for compounds and compositions that provide the primary benefit of improved durability of the hair set.

The use of resins, or polymers, in hair sprays is well known, as summarized in Grollier et al. U.S. Pat. No. 4,445,521. The resins conventionally used in hair sprays are linear vinyl (e.g., an alkyl vinyl ether) or acrylic (e.g., an alkyl acrylate) polymers prepared by copolymerizing two or more monomers in a free radical polymerization reaction. The vinyl and acrylic-based resins are used in relatively high concentrations in a hair spray composition to fix the hair in a particular configuration and to provide good hair set retention. However, at high concentrations, the vinyl and acrylic-based resins exhibit disadvantages that adversely affect the hair, such as poor combing and feel, and excessive stiffness, crust, and flaking.

The vinyl and acrylic-based hair fixative resins typically used in hair sprays were designed for use in anhydrous alcoholic hair spray compositions. The resins, therefore, had excellent compatibility with, and solubility in, alcohols (e.g., ethanol) used in pump spray compositions and hydrocarbons used as propellants in aerosol compositions. However, due to environmental and toxicological concerns, government regulations require a decreased amount of organic solvents in hair sprays and related compositions. Therefore, the alcohols and the hydrocarbon gases traditionally present in hair spray compositions are being replaced with water and water-soluble solvents, like dimethyl ether, that pose less harm to the environment.

The solvent changes required by government regulation made many of the traditional vinyl and acrylic-based resins unsuitable in hair spray compositions. For example, the solubility of the traditional resins in water or hydroalcoholic solvents is poor, and the presence of water in the hair spray composition increases the viscosity of the composition, thereby making spraying difficult to impossible. The relatively high viscosity of the compositions, therefore, requires a reduction in the resin concentration of the composition, which, in turn, results in insufficient hair set retention. The presence of water also increases the tackiness of the resin on the hair, thereby prolonging the drying time of the hair spray on the hair. Water also reduces the hair-wetting ability of the compositions, resulting in beading and flaking of the resin from the hair. In the case of aerosol products, the combination of water, resin, and propellant gas results in poor delivery and foaming of the composition, large aerosol particle size, and beading of the resin.

The need to change solvent systems for hair sprays again led investigators to search for new hair setting resins, and hair setting compositions, that overcome the disadvantages associated with the vinyl and acrylic resins. As set forth in European Patent Application 0 619 111, one class of resins is the polyurethanes. It would be desirable to provide an aqueous hair spray composition containing a low amount of volatile organic compounds (VOC) that overcomes that disadvantages associated with prior hair setting compositions, while utilizing the traditional vinyl and acrylic resins.

SUMMARY OF THE INVENTION

The present invention is directed to aerosol and nonaerosol (i.e., pumpable) hair spray compositions containing: (a) a hydrophilic, carboxylated polyurethane resin, and (b) a second hair fixative resin. The second hair fixative resin is a traditional hair setting resin, such as a vinyl or acrylic resin. The second hair fixative resin is different from the carboxylated polyurethane resin, and can be an anionic, cationic, or nonionic resin because each class of resin is compatible with the carboxylated polyurethane resin, which does not require neutralization with a base.

The hair spray compositions impart good hair set retention and natural feel to sprayed hair, and provide superior hairstyle retention at high relative humidity. The carboxylated polyurethane resins are soluble in water and in a wide range of water-to-alcohol ratios, without the need to neutralize the resin with a base. The polyurethane resins also assist in solubilizing the second hair fixative resin in the water or hydroalcoholic solvent. Compositions containing the carboxylated polyurethane have a low viscosity. Therefore, the present hair spray compositions contain a low amount of VOC, are safe to the environment, and can be applied effectively.

In particular, the present invention is directed to hair spray compositions comprising: (a) about 0.25% to about 6%, by total weight of the composition, of a carboxylated polyurethane resin, (b) about 0.25% to about 6%, by total weight of the total composition, of a second hair fixative resin, (c) 0% to about 80%, by total weight of the composition, of an alcohol, like ethanol, and (d) about 15% to about 80%, by total weight of the composition, of water. The hair spray compositions have a pH of about 6 to about 10. In a preferred embodiment, the weight ratio of the second hair fixative resin to the carboxylated polyurethane resin is about 1 or less, i.e., about 0.04 to about 1.

The composition can be applied to the hair as a pump spray. Alternatively, if an aerosol composition is desired, the composition can further comprise about 5% to about 30%, by total weight of the composition, of a propellant. Optional ingredients also can be incorporated into the hair spray composition.

The polyurethane resin, also termed a polycarbamyl polyglycol, has pendant carboxyl groups and is hydrophilic. The polyurethane resins have good tear strength, excellent washability, good adhesion, and are soluble in water and polar solvents, thereby making them useful in hair spray compositions. The ability of a carboxylated polyurethane resin to impart good hair set retention properties to hair is unexpected. Traditional hair fixative resins are hydrophobic in order to prevent the absorption of water and destruction of the hair set. In contrast, the polyurethane resins are hydrophilic, and have the ability to absorb water and give the hair a soft, nontacky, natural feel, while also imparting good hair set retention properties to sprayed hair.

In addition, the polyurethane resins, alone and in combination with the second hair fixative resin, form clear, low viscosity solutions in neutral to slightly basic aqueous solvents. Compositions containing the hydrophilic polyurethane resins, therefore, are sprayable. The carboxylated polyurethane resins form elastic films that give treated hair a natural feel, and the second hair fixative resin gives treated hair a desired degree of stiffness.

In accordance with an important aspect of the present invention, the present hair spray compositions exhibit excellent sprayability when the viscosity of a 55% by weight VOC composition is about 1 to about 10 centipoise (cps), or about 1 to about 25 cps for an 80% by weight VOC composition. Compositions having such a viscosity provide a spray particle size of about 20 to about 150 microns.

The hair spray compositions can be designed to impart a natural feel, a conditioned feel, or a stiff feel to treated hair by a judicious selection: (a) of the second hair fixative resin, and (b) of the weight ratio of carboxylated polyurethane resin to second hair fixative resin. The hair spray compositions have a very low viscosity for excellent delivery properties, then gel on the hair after application because of the associative nature of the carboxylated polyurethane resin. The traditional second hair fixative resin is included in the composition to impart a desired degree of stiffness to treated hair, i.e., to give the consumer a "signal" that a hair fixative resin is on the hair, and to reduce crust and flaking. The hair spray compositions, therefore, impart superior hair set retention and feel to treated hair.

In accordance with another important aspect of the present invention, the hair spray compositions exhibit improved washability from treated hair when the carboxylated polyurethane resin has an acid value of at least 7 mg KOH/g (milligram potassium hydroxide per gram of resin), and preferably about 7 to about 50 mg KOH/g of resin. The polyurethane resins do not require neutralization with a base to provide a useful hair spray composition.

In accordance with one embodiment of the present invention, the carboxylated polyurethane resin used in the hair spray composition is produced by reacting: (a) a diol component comprising a polyoxyalkylene diol; (b) an alkylene glycol; (c) a diisocyanate; (d) water in an amount of about 0.1% to about 0.5% of the combined weight of (a), (b), (c), and (e); and (e) a 2,2-di(hydroxymethyl)alkanoic acid, preferably 2,2-di(hydroxymethyl)propionic acid, wherein the ratio of NCO (isocyanate) groups to OH (hydroxyl) groups in the water, diol, and glycol, i.e., the R-value, is about 0.5 to about 0.9.

The hydrophilic carboxylated polyurethane resin contains polyoxyalkylene units, i.e., soft segments, and/or alkylene units, i.e., hard segments, connected by urethane linkages. Preferably, the carboxylated polyurethane resin contains soft and hard segments. Also incorporated into the polymer chain is a small amount of a diol having a pendant carboxyl group. The polymer chain also contains urea linkages resulting from a reaction between the water and isocyanate groups, which modify the hair styling properties of the carboxylated polyurethane resin.

Polyoxyethylene soft segments of the polyurethane resin impart hydrophilicity to the polyurethane. Soft segments derived from polyoxypropylene and polyoxytetramethylene diols provide a softer, but less hydrophilic, polyurethane. Hydrophilic polyurethane resins having improved strength and superior adhesive properties can be formed by using combinations of polyoxyalkylene diols.

In another embodiment of the present invention, the carboxylated polyurethane resins used in the hair spray composition are produced from (a) a major portion of polyoxyethylene diol having a molecular weight of 6000 to 10,000; (b) an alkylene glycol, preferably diethylene glycol, cyclohexanedimethanol, or dipropylene glycol; (c) a diisocyanate; (d) water in the amount of about 0.1% to about 0.5% by weight; and (e) a 2,2-di-(hydroxymethyl)alkanoic acid, wherein the ratio of NCO to OH in the water, diol, and glycol mixture (i.e., the R-value) is about 0.5 to about 0.9. These polyurethane resins are soluble in dilute (neutral to basic) aqueous solutions, and exhibit good sprayability, superior feel, low flaking, desirable crust, and good set retention when applied to hair. The polyurethane resins are hydrophilic, and provide a soft feel in a hydrated state. In a particular embodiment of a polyurethane resin produced with a major portion of polyoxyethylene diol, water is added in the amount of about 0.1% to about 0.4% by weight, and the ratio of NCO to OH of the water, diol and glycol mixture (i.e., the R-value) is about 0.55 to about 0.85 to provide a carboxylated polyurethane resin having improved adhesiveness to the hair and improved slip, i.e., improved combing properties.

Another aspect of the present invention is to provide a hair spray composition that provides good hair set retention at high relative humidity and that imparts a soft, natural feel to sprayed hair. Accordingly, a hydrophilic polyurethane resin incorporated into a present hair spray composition has a weight average molecular weight of about ($M_w$) of about 10,000 to about 80,000, preferably 15,000 to about 75,000, and to achieve the full advantage of the present invention about 15,000 to about 50,000. The polyurethane resins also have a polydispersibility index (PDI) of about 1 to about 4, and preferably about 1 to about 3. Preferred polyurethane resins have an R-value of about 0.65 to about 0.85.

In accordance with another important aspect of the present invention, the carboxylated polyurethane resin modifies the properties of the second hair setting resin to provide a low viscosity, low VOC composition that can be easily applied to the hair and gives hair a natural feel through a stiff feel, as desired, while imparting good set retention properties, without forming a crust or flaking.

DETAILED DESCRIPTION OF THE INVENTION

The present hair spray compositions are sprayable hair styling aids containing a carboxylated polyurethane resin and a second hair setting resin. The polyurethane resins are soluble in a broad range of water/alcohol mixtures and help solubilize the second hair setting resin, thereby permitting the preparation of aerosol and nonaerosol, i.e., pump spray, compositions containing a reduced amount of volatile organic compounds (VOC). The hair spray compositions also can contain propellant gases for application as an aerosol spray. The carboxylated polyurethane resins also possess thermal properties that allow styling of the hair with curling irons and blow dryers. The present hair spray compositions, therefore, overcome problems and disadvantages associated with compositions which contain only a traditional acrylic or vinyl-based hair fixative resin, and provide improved styling, hair set retention, hair feel, washability, and spray properties.

In particular, the present hair spray compositions comprise about 0.25% to about 6%, and preferably about 0.5% to about 5%, by total weight, of a carboxylated polyurethane resin. To achieve the full advantage of the present invention, the composition comprises about 1% to about 5%, by weight of the composition, of a carboxylated polyurethane resin.

The polyurethane resins are linear, hydroxyl-terminated copolymers having pendant carboxyl groups, and preferably pendant carboxylic acid groups. The hydrophilic polyurethanes typically are ethoxylated and/or propoxylated at least at one terminal end. In accordance with an important feature of the present invention, the polyurethane resins can be solubilized in water, or in a hydroalcoholic solution, in the absence of a base.

The carboxylated polyurethane resins are soft and flexible, and have a melting point of about 40° C. to about 100° C., and preferably about 45° C. to about 90° C. To achieve the full advantage of the present invention, the polyurethane resins have a melting point of about 50° C. to about 85° C.

The carboxylated polyurethane resins provide treated hair with a conditioned, soft and natural feel, while maintaining good style retention. The carboxylated polyurethane resins also have physical properties which make them suitable for use in hair sprays. For example, the carboxylated polyurethane resins are (a) sprayable, (b) soluble in hydroalcoholic solutions, (c) propellant tolerant, and (d) fast drying. The polyurethane resins also exhibit good wet combing properties, and are washable from the hair.

The hydrophilic polyurethanes are prepared using an aliphatic diisocyanate, an aromatic diisocyanate, or a mixture thereof. An aliphatic diisocyanate is preferred. The diisocyanate is typically interacted with a low molecular weight glycol or triol, such as ethylene glycol, diethylene glycol, propylene glycol, glycerol, hexylene glycol, cyclohexanediol, cyclohexanedimethanol, 1,4-butanediol, tripropylene glycol, triethylene glycol, dipropylene glycol, or mixtures thereof, wherein the glycol or triol has at least two hydroxyl groups and a molecular weight up to about 200, to provide a polyurethane. The diisocyanate also can be reacted with a polymeric dihydroxy-terminated oligomer, e.g., a polyoxyalkylene glycol having a molecular weight of about 200 to 10,000 to provide a hydrophilic polyurethane. Exemplary oligomers include, but are not limited to, polypropylene glycols, polyethylene glycols, ethylene glycol-propylene glycol copolymers, polybutylene glycols, and mixtures thereof. Preferably, a diisocyanate is interacted both with a low molecular weight diol or triol and with an oligomer to provide a hydrophilic polyurethane.

Exemplary, but nonlimiting, diisocyanates include trimethylhexamethylene diisocyanate, isophorone diisocyanate, decamethylene-1,10-diisocyanate, cyclohexane-1,2-diisocyanate, methylene bis(cyclohexyl-4-isocyanate), toluene-1,4-diisocyanate, toluene-2,6-diisocyanate, diphenylmethane-4,4'-diisocyanate, 3,3'-dimethyldiphenylmethane-4,4'-diisocyanate, m-phenylene diisocyanate, p-phenylene diisocyanate, chlorophenylene diisocyanate, hexamethylene-1,6-diisocyanate, tetramethylene-1,4-diisocyanate, cyclohexane-1,4-diisocyanate, naphthalene-1,5-diisocyanate, 1-methoxyphenyl-2,4-diisocyanate, 4,4'-biphenylene diisocyanate, 3,3'-dimethoxy-4,4'-biphenyl diisocyanate, 3,3'-dimethyl-4,4'-biphenyl diisocyanate, 3,3'-dichlorophenyl-4,4'-diisocyanate, 2,2',5,5'-tetrachlorodiphenyl-4,4'-diisocyanate, trimethylhexamethylene diisocyanate, m-xylene diisocyanate, and mixtures thereof.

The polyurethane resin contains pendant carboxyl groups to improve the water solubility or dispersibility of the polyurethane resin. The number of carboxylic acid groups is sufficient to give the polyurethane resin an acid value of at least about 7, and preferably about 7 to about 50, mg KOH/g resin. Examples of useful carboxylate polyurethanes are disclosed in Gould et al. U.S. Pat. No. 5,000,955, incorporated herein by reference. Other useful hydrophilic polyurethanes are disclosed in U.S. Pat. Nos. 3,822,238; 4,156,066; 4,156,067; 4,255,550; and 4,743,673, also incorporated herein by reference.

A polyurethane resin incorporated into a present hair spray composition preferably comprises a reaction product of a diol component, an alkylene glycol, an aliphatic diisocyanate, water, and a 2,2-di-(hydroxymethyl)alkanoic acid. Alternatively, an amine, such as diglycolamine, can be substituted for at least a portion of the water in the reaction mixture. Aqueous solutions of the hydrophilic carboxylated polyurethane resins have low viscosities, and impart a soft feel, good set retention, reduced flaking and crust, and improved hair setting and conditioning properties to sprayed hair.

In one embodiment, the polyurethane resin comprises the reaction product of: a diol component comprising a polyoxyalkylene diol, preferably a polyoxyethylene diol having a number average molecular weight ($M_n$) of about 200 to about 10,000, a polyoxypropylene diol having an $M_n$ of about 200 to about 2500, a block copolymer of ethylene oxide and propylene oxide having an $M_n$ of about 1,000 to about 9,000, or a polyoxytetramethylene diol having an $M_n$ of about 200 to about 4,000; about 0.01% to about 10% by weight of a low molecular weight alkylene glycol selected from the group consisting of ethylene glycol, propylene glycol, 2-ethyl-1,3-hexanediol, tripropylene glycol, triethylene glycol, 2,4-pentanediol, 2-methyl-1,3-propanediol, 2-methyl-1,3-pentanediol, cyclohexanediol, cyclohexanedimethanol, dipropylene glycol, diethylene glycol, and mixtures thereof; an organic diisocyanate; a 2,2-di-(hydroxymethyl)alkanoic acid; and water in an amount of about 0.1% to about 0.5% by weight of the reaction mixture, wherein the NCO/OH ratio (i.e., the R-value) is about 0.5 to about 0.9, and preferably about 0.55 to about 0.85. To achieve the full advantage of the present invention, the R-value is about 0.65 to about 0.85.

Alternatively, an amine can be used in the reaction mixture for at least a portion of the water. The amine can be added to the reaction mixture in an amount of about 0.01% to about 0.8% by weight amine, preferably about 0.02% to about 0.5% amine to about 0.1% to about 0.2% water in the reaction mixture. Amines that can be used in the reaction are ethylenediamine, propylenediamine, monoethanolamine, diglycolamine, and JEFFAMINE D1-230, D-400, D-2000, D-4000, ED-0600, ED-900, or ED-2001. The hydroxylamines and the JEFFAMINE products are manufactured by Texaco Chemical Company. Preferably, the amine is a hydroxylamine, and most preferably the amine is monoethanolamine and/or diglycolamine.

The polyoxyethylene diols are available from Union Carbide Corporation under the trademark CARBOWAX, such as CARBOWAX® 1450 and CARBOWAX® 8000 wherein the number represents number average molecular weight. The polyoxypropylene diols (PPG) are available from various sources, such as the PPG series of ARCO NIAX® PPG 1025, PPG 425, PPG 725, PPG 1225, and PPG 2025, and as R2134 (2200) and R2135 (4400), wherein the number represents number average molecular weight. Triols are also available from ARCO as NIAX® Polyols 11-34, LG-650, LG-56, LG-168, LHT-28, LHT-240. The polyoxytetramethylene diols are available from E. I. DuPont de Nemours as TERATHANE 600, 1000, 1400, 2000, and 2900. Polyetherpolycarbonate is available from BASF under the tradename polytetrahydrofuran 1000 CD and 2000 CD.

A block polyoxyalkylene polymer also can be used in the reaction. For example, a propylene oxide terminated block of ethylene glycol manufactured by BASF under the tradename PLURONIC R and a ethylene oxide terminated block of propylene glycol manufactured by BASF under the tradename of PLURONIC can be used for the polyoxyalkylene in the reaction. Examples of the block copolymers of the sequential addition of ethylene oxide and propylene oxide to ethylene diamine are made by BASF under the tradename of PLURONIC, such as PLURONIC F68, F64, F127, L35, L92, L82, 17R2, and 25R2.

Preferably, the polyoxyalkylene diol used in forming the hydrophilic polyurethane resin is polyoxyethylene diol. The blends of polyoxyalkylene diols contain at least about 10% polyoxyethylene diol, preferably, at least 20% polyoxyethylene diol, and most preferably, at least 25% polyoxyethylene diol, by weight.

The amount of polyoxyalkylene diol having a molecular weight of 200 to 10,000 in the polyurethane resin can vary from about 10% to about 90%, preferably about 30% to about 90%, and most preferably about 40% to about 90%, by weight, and the number average molecular weight ($M_n$) of the polyoxyalkylene diol can vary from about 200 to about 10,000, preferably from about 400 to about 9,500, and more preferably from about 800 to about 9,000.

The alkylene glycols can be purchased from numerous sources. For example, propylene glycol can be purchased from Aldrich Chemical Company as 1,2-propanediol. The amount of the alkylene glycol (hard segment) component in the polyurethane resin can be about 0.01% to about 20%, preferably about 0.05% to about 15%, more preferably about 0.1% to about 12%, still more preferably about 0.5% to about 10%, and most preferably about 1.0% to about 8%, by weight of the reaction mixture.

The diisocyanate in the reaction mixture can be an aliphatic diisocyanate, an aromatic diisocyanate, or a mixture thereof. The aliphatic diisocyanates are preferred. An especially preferred diisocyanate is methylene bis(cyclohexyl-4-isocyanate). Other examples of diisocyanates are trimethyl hexamethylene diisocyanate and isophorone diisocyanate. Representative examples of the preferred aliphatic diisocyanates include, but are not limited to tetramethylene diisocyanate, hexamethylene diisocyanate, trimethylene diisocyanate, trimethylhexamethylene diisocyanate, cyclohexyl-1,2-diisocyanate, and cyclohexyl-1,4-diisocyanate. Examples of aromatic diisocyanates include 2,4-toluene diisocyanate and 2,6-toluene diisocyanate. Also suitable are the isocyanate equivalents which form urethane linkages, exemplified by nitrile carbonates, such as adiponitrile carbonate of U.S. Pat. No. 4,810,543, incorporated herein by reference. The amount of diisocyanate varies from about 3% to about 80%, preferably from about 4% to about 70%, more preferably from about 5% to about 60%, still more preferably from about 6% to about 55%, and most preferably from about 6.5% to about 50%, by weight. The polyurethane resins are prepared by reacting the polyoxyalkylene diols with the diisocyanates.

The amount of water in the reaction mixture is about 0.1% to about 0.5%, and more preferably about 0.15% to about 0.45%, by weight, of the reaction mixture.

In another embodiment, the hydrophilic polyurethane resin comprises a reaction product of: (a) a diol having a major portion of a polyoxyethylene diol having an $M_n$ of 6,000 to 10,000, and a minor portion of a polyoxypropylene diol having an $M_n$ of about 1,000 to about 3,500 or a polyoxyethylene diol having an $M_n$ of about 400 to about 2000; (b) an alkylene glycol; (c) a diisocyanate; (d) water in an amount of about 0.1% to about 0.5% by weight of the reaction mixture; and (e) a 2,2-di(hydroxymethyl)alkanoic acid, and an equivalent mole weight ratio of NCO to OH of the water, diol and glycol of about 0.5 to about 0.9. Preferably at least 45% of the polyoxyethylene glycol of $M_n$ about 8000, more preferably at least about 55%, still more preferably at least about 65%, and most preferably at least 75%, by weight, is used in the total reaction mixture. The amount of the lower molecular weight polyoxyethylene diol having an $M_n$ of about 400 to about 2,000 is about 1% to about 15%, and preferably from about 2% to about 10%, by weight of the reaction mixture. Preferably, the alkylene glycol is diethylene glycol, cyclohexanedimethanol, dipropylene glycol, or a mixture thereof.

The 2,2-di-(hydroxymethyl)alkanoic acid preferably is dimethylolpropionic acid. The amount of dimethylolpropionic acid is about 1% to about 8%, preferably about 1.5% to about 7%, and most preferably about 2% to about 6% by weight of the reaction mixture. The final product has an acid value of at least about 7 mg KOH/g resin. To achieve the full advantage of the invention, the carboxylated polyurethane resin has an acid value of about least 7 to about 50 mg KOH/g resin. The sum of all ingredients, including the diols, glycols, water, and diisocyanate in the reaction mixture totals 100% by weight.

Alternatively, an amine can be used in place of a portion of the water in the reaction mixture. An amount of about 0.15% to about 0.6% by weight amine, based on diglycolamine, is used with about 0.1% to about 0.5% by weight water, more preferably about 0.1% to about 0.40% of water, and most preferably of about 0.15% to about 0.3% of water.

The preferred diol is a polyoxyethylene diol, preferably a polyoxyethylene diol of $M_n$ about 400 to about 5,000. The preferred water level is about 0.01% to about 0.65%, preferably about 0.02% to about 0.60%, more preferably about 0.05% to about 0.55%, and most preferably about 0.10% to about 0.50%, by weight.

The ratio of NCO to OH groups from the diol, alkylene glycol, amines and water (i.e., the R-value) in the reaction mixture is about 0.5 to about 0.9, preferably about 0.55 to about 0.85, and most preferably about 0.65 to about 0.85. The weight average molecular weight ($M_w$) of the carboxylated polyurethane resin is about 10,000 to about 80,000, preferably about 15,000 to about 75,000, and most preferably about 15,000 to about 50,000.

The carboxylated polyurethane resins of this embodiment are especially useful in hair spray compositions because the polyurethane resin is soluble in ethanol/water mixtures, and in dilute neutral to basic aqueous solutions, to form low viscosity solutions. Solutions of the polyurethane resins also exhibit improved sprayability, improved feel of sprayed hair, low flaking and crust, and improved set retention of the hair. The carboxylated polyurethane resins maintain these advantageous properties when admixed with a second hair fixative resin, and improve the properties of the second hair fixative resin, e.g., increased water solubility, decreased solution viscosity, improved hair feel, and reduced crust and flaking.

For hair spray compositions, the hydrophilicity of the polyurethane resin is an unexpected important property in combination with other desirable properties, such as washability. Conventional hair fixative resins are hydrophobic materials that impart a stiff feel to the hair. The present polyurethane resins are hydrophilic, which gives the hair a soft, natural feel, yet are adhesive to the hair and impart excellent hair set retention. A combination of a carboxylated polyurethane resin and a second hair fixative resin allows a formulator to design a hair spray composition that imparts a desired level of stiffness to the hair. It also has been found that the hair styling properties of the polyurethane resin can be effected by small changes in the amount of water, the ratio of NCO/OH, and the amount of the di(hydroxymethyl) alkanoic acid in the reaction mixture.

Further, the weight average molecular weight of the carboxylated polyurethane resins can be decreased or increased by modifying the amount of water in the reaction mixture within a predetermined range. The above-described polyurethane resins have an $M_w$ of about 10,000 to about 80,000, and preferably about 15,000 to about 75,000; and a kinematic viscosity at 3 wt. % in 55/42 ethanol/water (by weight) of about 1 to about 40 centistokes (cs), formed from a range of water of about 0.1% to about 0.4% by weight of the reaction mixture, a NCO/OH ratio (i.e., R-value) of about 0.75 to about 0.85, and a range of dimethylolpropionic acid of about 2% to about 6% by weight of the reaction mixture.

A polyurethane resin having an $M_w$ of less than about 25,000 can be formed using a water level of about 0.25% to about 0.40% by weight of the reaction mixture, a ratio of NCO/OH about 0.60 to about 0.75, and a range of dimethylolpropionic acid of about 3.0% to about 6.5% by weight of the reaction mixture. The polyurethane resin has a kinematic viscosity at 3 wt. % in a 55/42 ethanol/water solution (by weight) of about 1 to about 20 cs. These polyurethane resins are useful as hair styling aids and form low viscosity solutions in water and hydroalcoholic solutions.

Polyurethane resins prepared using an amount of water of about 0.1% to about 0.4% by weight in the reaction mixture, and a NCO/OH ratio of about 0.5 to about 0.9, preferably from about 0.6 to about 0.7, have a set retention after 30 minutes of about 80% to about 90%. An amount of water of about 0.15% to about 0.45% by weight in the reaction mixture and a NCO/OH ratio of about 0.6 to about 0.9, preferably from about 0.7 to about 0.9, can be used to provide polyurethane resins having a set retention of about 85% to about 98% after 30 minutes.

Alternatively, small amounts of diglycolamine can be substituted for water in the reaction mixture, e.g., about 0.02% to about 1%, preferably about 0.03% to about 0.75%, more preferably about 0.04% to about 0.5%, and most preferably 0.05% to about 0.4% diglycolamine, by weight, can be used in the reaction mixture.

The alkylene glycol used in this embodiment can be, for example, ethylene glycol, diethylene glycol, propylene glycol, dipropylene glycol, cyclohexanediol, 1,4-butanediol, cyclohexanedimethanol, tripropylene glycol, or triethylene glycol; preferably diethylene glycol, cyclohexanedimethanol, or dipropylene glycol; and most preferably diethylene glycol. The amount of the alkylene glycol (hard segments) in the reaction mixture is about 0.01% to about 20%, preferably about 0.05% to about 15%, more preferably about 0.1% to about 12%, still more preferably about 0.5% to about 10%, and most preferably about 1% to about 5%, by weight.

For hair spray compositions, the kinematic viscosity of a solution of a polyurethane resin and a second hair fixative resin having a weight ratio of ethanol/water/total resin of 55/42/3 is less than about 1,000 centistokes (e.g., about 1 to about 1000 cs), preferably about 500 cs or less, more preferably about 100 cs or less, still more preferably less than about 50 cs, and most preferably less than about 40 cs.

In each embodiment, the polyurethane-forming reaction is catalyzed by known catalysts. Tin-containing catalysts, such as tin salts or organotin esters, for example, stannous octoate and dibutyltin dilaurate, or tertiary amines, such as triethylene diamine and N,N,N',N'-tetramethyl-1,3-butane diamine, are preferred. The catalyst is used in an amount effective to catalyze the reaction, i.e., about 0.001 to 1 weight percent of the total weight of the reactive components. Reaction temperature is about 40° C. to about 120° C.

In addition to the carboxylated polyurethane resin, the hair spray composition contains about 0.25% to about 6%, and preferably about 0.5% to about 5%, by weight, of a second hair fixative resin. To achieve the full advantage of the present invention, the hair spray composition contains about 1% to about 5%, by weight of the composition of a second hair fixative resin. Preferably, the weight ratio of the second hair fixative resin to the carboxylated polyurethane resin in the composition is about one or less, i.e., about 0.04 to about 1. The second hair fixative resin can be a nonionic, cationic, or anionic resin, because the carboxylated polyurethane resin is compatible with each class of resins. It also is envisioned that the second hair fixative resin is a mixture of two or more hair fixative resins in a total amount of 0.25% to 6% by weight of the composition.

The second hair fixative resin preferably is a hydrophobic compound that retards the tendency of hair to absorb water. The second hair fixative resin also is a hard, brittle compound having a glass transition temperature of about 100° C. or greater, preferably about 110° C. or greater, e.g., up to 200° C. An important feature of the second hair fixative resin is to reduce flaking attributed to the carboxylated polyurethane resins, and to impart hair set properties that typically are associated with the second hair fixative resin.

In particular, the second hair fixative resin imparts a desired and predetermined degree of stiffness to the hair. In contrast, the carboxylated polyurethane resin provides an elastic film on the hair. However, consumers equate a good hair spray with a degree of hair stiffness. The present hair spray compositions, therefore, impart the desired stiffness to the hair, while further providing the benefits attributed to the polyurethane resin, such as a low viscosity, low VOC composition, reduced flaking, and a soft, natural hair feel.

Nonlimiting examples of second hair fixative resins useful in the present hair spray compositions can be found in Grollier et al. U.S. Pat. No. 4,445,521, incorporated herein by reference. Specific second hair fixative resins include, but are not limited to, acrylamide copolymers, acrylamide/sodium acrylate copolymer, acrylate/ammonium methacrylate copolymer, acrylate copolymers, acrylic/acrylate copolymers, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, ammonium acrylate copolymers, ammonium vinyl acetate/acrylate copolymers, AMP acrylate/diacetoneacrylamide copolymers, AMPD acrylate/diacetoneacrylamide copolymers, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dodecanedioic acid/cetearyl alcohol/glycol copolymer, ethyl ester of PVM/MA copolymer, isopropyl ester of PVM/MA copolymer, karaya gum, methacryloyl ethyl betaine/methacrylate copolymers, octylacrylamide/acrylate/butylaminoethyl methacrylate copolymers, octylacrylamide/acrylate copolymers, phthalic anhydride/glycerin/glycidyl decanoate copolymer, phthalic/trimellitic/glycol copolymers, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, vinyl acetate/crotonate copolymers, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof.

In addition to the carboxylated polyurethane resin and the second hair fixative resin, the hair spray composition contains 0% to about 80%, by total weight of the composition, of an alcohol. Preferably, the composition contains 0% to about 55%, by weight, of an alcohol. In order to reduce the adverse environmental affects attributed to volatile organic compounds, the amount of alcohol is maintained at as low a level as possible without adversely affecting the esthetics or efficacy of the hair spray composition.

The alcohol typically used in the hair spray composition is ethanol, although isopropyl alcohol also can be incorporated into the composition. The carboxylated polyurethane resins are readily solubilized in a wide range of hydroalcoholic solutions, without the addition of basic neutralizer, thereby permitting a decrease in the amount of alcohol present in the hair spray composition.

The hair spray composition also contains 15% to about 95%, by total weight of the composition, of water. The amount of water is maximized in order to reduce the amount of VOC in the composition. Because the carboxylated polyurethane resins are hydrophilic, it is not necessary to include a base in the water to neutralize and solubilize the polyurethane resin. The carboxylated polyurethane resin also assists in solubilizing the second hair fixative resin, and in reducing the viscosity of the hair spray composition.

Optional ingredients also can be incorporated into the hair spray composition. The identity of the optional ingredients is not limited as long as the optional ingredients do not adversely affect the esthetics or efficacy of the hair spray composition. For example, a hair spray composition containing only a polyurethane resin, a second hair fixative resin, water, and alcohol can be applied as a nonaerosol pump spray. The composition can be modified for application as an aerosol spray by incorporating about 5% to about 30%, by weight of the composition, of a propellant. The carboxylated polyurethane resin and second hair fixative resin tolerate the propellant gases commonly used in aerosol compositions, such as the alkanes and carbon dioxide.

The optional propellant gas included in the hair spray compositions can be any liquefiable gas conventionally used for aerosol products. Examples of compounds that are suitable for use as propellants are trichlorofluoromethane, dichlorodifluoromethane, dichlorotetrafluoroethane, monochlorodifluoromethane, trichlorotrifluoroethane, dimethyl ether, propane, n-butane, and isobutane, either singly or admixed. Water-soluble gases such as dimethyl ether, carbon dioxide, and/or nitrous oxide also can be used to obtain aerosol sprays having reduced flammability.

Water-immiscible, liquified, hydrocarbon and halogenated hydrocarbon gases such as propane, butane, and chlorofluorocarbons can be used advantageously to deliver the contents of an aerosol container without the dramatic pressure drops associated with other immiscible gases. The head space left inside the aerosol container is not a factor because the liquified gas sits on top of the aqueous composition and the pressure inside the container is maintained at the vapor pressure of the saturated hydrocarbon vapor.

Other insoluble, compressed gases such as nitrogen, helium, and fully fluorinated oxetanes and oxepanes also are useful to deliver the compositions from aerosol containers. If the propellant, such as dimethyl ether, incorporates a vapor pressure suppressant (e.g., trichloroethane or dichloromethane), the amount of suppressant is included as part of the propellant for weight percentage calculations.

The hair spray compositions also can contain a variety of other nonessential, optional components. Such conventional optional ingredients are well known to those skilled in the art, e.g., emulsifiers, such as anionic or nonionic surfactants; preservatives, such as benzyl alcohol, methyl paraben, propyl paraben, or imidazolidinylurea; cationic conditioners, such as cetyl trimethyl ammonium chloride, stearyl dimethyl benzyl ammonium chloride, and di(partially hydrogenated tallow) dimethyl ammonium chloride; coloring agents such as any of the FD&C or D&C dyes; perfume oils; and chelating agents such as ethylenediaminetetraacetic acid. These optional components generally are included individually at a level of 0% to about 5%, by weight of the total composition.

The aqueous formulations of the present invention also can contain conventional hair spray adjuvants in amounts which generally range from about 0% to about 2% by weight, and preferably 0% to 1% by weight. Among the additives which can be used are plasticizers such as glycols, phthalate esters, and glycerine, silicones, emollients, lubricants, and penetrants such as various lanolin compounds, protein hydrolysates and other protein derivatives, ethylene adducts and polyoxyethylene cholesterol.

The hair spray compositions of the present invention are prepared by simply admixing and dissolving the carboxylated polyurethane resin, the second hair fixative resin, and any optional ingredients into an aqueous or hydroalcoholic carrier. The resulting solution can be used in a pump spray, or can be pressurized by the addition of an aerosol propellant in accordance with methods well known in the art.

EXAMPLE A

Preparation of a Carboxylated Polyurethane Resin A

Polyoxyethylene diol having an $M_n$ of 8000 was heated under vacuum to 0.060% of water and 736 parts of the dried diol was added to 21 parts of diethylene glycol, 18 parts of dimethylolpropionic acid, and 2.84 parts of water. The mixture was heated with stirring until a homogeneous melt was obtained. Then, 139 parts of methylene bis-cyclohexyl-4-4'-diisocyanate were added. The NCO/OH ratio was 0.85. When the temperature reached about 64° C., 1.85 ml of dibutyltin dilaurate was added, and the mass was allowed to exotherm. The mass was heated at 100° C. for about one hour to complete formation of the polymer. The polyurethane resin had an $M_w$ of 76,000 and dissolved in a slightly basic 55/45 ethanol/water solution (wt/wt) at a concentration of 5 wt. % to give a viscosity of 18 cps. The polyurethane resin had an acid value of 7.75 mg KOH/g resin, and a kinematic viscosity of 14.7 cs in 55/42/3 ethanol/water/polymer solution by weight.

EXAMPLE B

Preparation of Polyurethane Resin B

Polyoxyethylene diol having an $M_n$ of 8000 was heated under vacuum to 0.215% of water, and 736 parts of the dried diol was added to 21 parts of diethylene glycol, 59 parts of dimethylolpropionic acid, and 1.81 parts of water. The mixture was heated with stirring until a homogeneous melt was obtained. Then, 168 parts of methylene bis-cyclohexyl-4-4'-diisocyanate were added. The NCO/OH ratio was 0.65. When the temperature reached about 70° C., 1.85 ml of dibutyltin dilaurate was added, and the mass was allowed to exotherm. The mass was heated at 100° C. for about one hour to complete formation of the polyurethane resin. The polyurethane resin had an $M_w$ of 15,000 and dissolved in slightly basic 55/45 ethanol/water (wt/wt) solution at a concentration of 5 wt. % was clear and had a viscosity of 10 cps. The polyurethane resin had an acid value of 24.22 g KOH/g resin, and a kinematic viscosity of 4.60 cps in 55/42/3 ethanol/water/polymer solution by weight. The polyurethane resin was used in a hair spray composition to give a superior and natural soft feel, excellent set retention, low crust, and low flaking properties to treated hair. Polyurethane Resin B had a crust rating of 4.5, a feel of 4.5, a flaking rating of 1.8, a set retention of 85% at 30 minutes.

EXAMPLE C

Preparation of Polyurethane Resin C

Polyoxyethylene diol having an $M_n$ of 8000 was heated under vacuum to 0.060% of water, and 736 parts of the dried diol was added to 21 parts of diethylene glycol, 18 parts of dimethylolpropionic acid, and 0.96 part of water. The mixture was heated with stirring until a homogeneous melt was obtained. Then, 114 parts of methylene bis-cyclohexyl-4-4'-diisocyanate were added. The NCO/OH ratio was 0.85. When the temperature reached about 63° C., 1.85 ml of dibutyltin dilaurate was added, and the mass was allowed to exotherm. The mass was heated at 100° C. for about one hour to complete formation of the polyurethane resin. The polyurethane resin dissolved in slightly basic 55/45 ethanol/water solution (wt/wt) at a concentration of 5 wt. % was clear and had a viscosity of 14 cps. The polyurethane resin had an acid value of 8.01 mg KOH/g resin, and an $M_w$ of 40,000. The polyurethane resin was used in a hair spray composition to impart a superior soft feel, excellent set retention, low crust, and low flaking properties to treated hair. Polyurethane Resin C provided a crust rating of 4.9, a feel of 6.7, a flaking rating of 7, a set retention of 97% at 30 minutes, and a set retention of 95% at 60 minutes.

EXAMPLE D

Preparation of Polyurethane Resin D

A batch of 13,147 parts of polyoxyethylene diol having an $M_n$ of 8000 was added to a five-gallon electrically heated reactor and heated under vacuum to dry the glycol. The dried diol was added to 368 parts of diethylene glycol and 321 parts of dimethylolpropionic acid, and the mixture was heated to 105° C. in order to melt the ingredients. The mixture was allowed to cool to about 175° F. to about 185° F. and the water level was analyzed by Karl Fisher method as 0.0675%. Then, 19.41 grams of water was added to the mixture to bring the total water to 28.75 grams of water.

A separate reactor contained 2073 parts of methylene bis(cyclohexyl-4-isocyanate). To the diols was added 33.04 cc of dibutyltin dilaurate. Then the isocyanate was heated to about 110°–115° F., and both liquids were forced out under nitrogen pressure using a piston cylinder at about a ratio of 0.1492. Twelve shots of liquid were pumped into a polypropylene tub and heated for one hour at 100° C. The NCO/OH ratio was 0.85.

The polyurethane resin was dissolved at 3 wt. % solids in 55/45 ethanol/water solution (wt/wt) and gave viscosities of 11 cps using a Brookfield viscometer. The polyurethane resin had a kinematic viscosity of 7.67 cps in 55/42/3 ethanol/water/polymer solution by weight. The polymer had an $M_w$ of 40,000, and was very similar to Polyurethane Resin C.

The polyurethane resin was used in a hair spray composition to give a superior soft and natural feel, excellent set retention, low crust, and low flaking properties to treated hair.

EXAMPLE E

Preparation of Polyurethane Resin E

A batch of 13,147 parts of polyoxyethylene diol having an $M_n$ of 8000 was added to a five-gallon electrically heated reactor and heated under vacuum to dry the glycol. The dried diol was added to 368 parts of diethylene glycol and 321 parts of dimethylolpropionic acid, and the mixture was heated to 105° C. in order to melt the ingredients. The mixture was allowed to cool to about 175° F. to about 185° F. and a sample of the mixture was taken and analyzed for its water content by Karl Fisher method. The mixture had a water content of 0.0625% water and 26.66 grams of water was added to the mixture to bring the total water to 35.31 grams of water.

A separate reactor contained 2162 parts of methylene bis(cyclohexyl-4-isocyanate). To the diols was added 33.04 cc dibutyltin dilaurate. Then the diisocyanate was heated to about 110°–115° F., and both liquids were forced out under nitrogen pressure using a piston cylinder at about a ratio of 0.1555. Twelve shots of liquid were pumped into a polypropylene tub and heated for one hour at 100° C. The NCO/OH ratio was 0.85.

The polyurethane resin was dissolved at 3% solids in 55/45 ethanol/water solution (wt/wt) and gave a viscosity of 11.5 cps using a Brookfield viscometer. The polyurethane resin had a kinematic viscosity of 9.81 cs in 55/42/3 ethanol/water/polymer solution by weight, and an $M_w$ of 49,000. Polyurethane Resin E was similar to Polyurethane Resins C and D.

EXAMPLE F

Preparation of Polyurethane Resin F

Polyoxyethylene diol having an $M_n$ of 8000 was heated under vacuum to 0.060% of water, and 336 parts of the dried diol was added to 9.3 parts of diethylene glycol, 27 parts of dimethylolpropionic acid, 8.2 parts of diglycolamine and 0.002 part of water. The mixture was heated with stirring until a homogeneous melt was obtained. Then, 73 parts of methylene bis-cyclohexyl-4-4'-diisocyanate were added. The NCO/OH ratio was 0.65. When the temperature reached about 65° C., 0.92 ml of dibutyltin dilaurate was added, and the mass was allowed to exotherm. The mass was heated at 100° C. for about one hour to complete formation of the polymer. The polyurethane resin dissolved in slightly basic 55/45 ethanol/water solution (wt/wt) at a concentration of 5 wt. % was clear. The polyurethane resin had an $M_w$ of 26,000, and a kinematic viscosity of 5.93 cs in 55/42/3 ethanol/water/polymer solution by weight.

EXAMPLE G

Preparation of Polyurethane Resin G

Polyoxyethylene diol having an $M_n$ of 8000 was heated under vacuum to 0.061% of water, and 736 parts of the dried diol was added to 21 parts of diethylene glycol, 59 parts of dimethylolpropionic acid, and 1.11 part of water. The mixture was heated with stirring until a homogeneous melt was obtained. Then, 185 parts of methylene bis-cyclohexyl-4-4'-diisocyanate were added. The NCO/OH ratio was 0.85. When the temperature reached about 63° C., 1.85 ml of dibutyltin dilaurate was added, and the mass was allowed to exotherm. The mass was heated at 100° C. for about one hour to complete formation of the polymer. The polyurethane resin had an $M_w$ of 21,000 and dissolved in slightly basic 55/45 ethanol/water solution (wt/wt) at a concentration of 5 wt. % was clear and had a viscosity of 10 cps. The polyurethane resin had a kinematic viscosity of 6.15 cps in 55/42/3 ethanol/water/polymer solution by weight. The polyurethane resin was used in a hair spray composition, and imparted a crust rating of 6.3, a feel of 8.1, a flaking rating of 8.3, a set retention of 81% at 30 minutes, and a set retention of 68% at 60 minutes to treated hair.

EXAMPLE H

Preparation of Polyurethane Resin H

Polyoxyethylene diol having an $M_n$ of 8000 was heated under vacuum to 0.156% of water and 756 parts of the dried diol was added to 21 parts of diethylene glycol, 39 parts of dimethylolpropionic acid, and 0.25 part of water. The mixture was heated with stirring until a homogeneous melt was obtained. Then, 136 parts of methylene bis-cyclohexyl-4-4'-diisocyanate were added. The NCO/OH ratio was 0.75. When the temperature reached about 66° C., 1.85 ml of dibutyltin dilaurate was added, and the mass was allowed to exotherm. The mass was heated at 100° C. for about one hour to complete formation of the polymer. The polyurethane resin ($M_w$ of 24,000) dissolved in a slightly basic 55/45 ethanol/water solution (wt/wt) at a concentration of 5 wt. % to produce a clear solution with a viscosity of 13 cps. Polyurethane Resin H was used in a hair spray composition. The polyurethane resin imparted a crust rating of 6.9, a feel of 5.5, a set retention of 95% at 30 minutes and a set retention of 90% at 60 minutes to treated hair.

EXAMPLE I

Preparation of Polyurethane Resin I

Polyoxyethylene diol having an $M_n$ of 8000 was heated under vacuum to 0.032% of water and 736 parts of the dried diol was added to 21 parts of diethylene glycol, 18 parts of dimethylolpropionic acid, and 2.06 parts of water. The mixture was heated with stirring until a homogeneous melt was obtained. Then, 113 parts of methylene bis-cyclohexyl-4-4'-diisocyanate were added. The NCO/OH ratio was 0.75. When the temperature reached about 65° C., 1.85 ml of dibutyltin dilaurate was added, and the mass was allowed to exotherm. The mass was heated at 100° C. for about one hour to complete formation of the polymer. The polyurethane resin dissolved in a slightly basic 55/45 ethanol/water solution (wt/wt) at a concentration of 5 wt. % to produce a clear solution with a viscosity of 13 cps. The polyurethane resin ($M_w$ 35,000) had a kinematic viscosity of 6.50 cs in 55/42/3 ethanol/water/polymer by weight solution. Polyurethane Resin I was used in a hair spray composition. The polyurethane resin imparted a crust rating of 4.2, a feel of 4.8, a flaking rating of 4.2, a set retention of 86% at 30 minutes, and a set retention of 73% at 60 minutes to treated hair.

To demonstrate the hair spray compositions of the present invention, several aerosol compositions containing 55% to 80% VOC (i.e., VOC is the sum of ethanol and dimethyl ether propellant) were prepared. Each composition contained 30% by weight dimethyl ether (i.e., DME), but the relative amounts of the carboxylated polyurethane resin (i.e., Polyurethane Resin B), and the second hair fixative resin were varied. The compositions are summarized below as Examples 1–30 in TABLES 1 and 2.

Each composition was prepared by dissolving the carboxylated polyurethane resin and the second hair fixative resin in a mixture of water and ethanol at room temperature. The resulting solutions then were placed in a standard aerosol can which was capped with a valve. The DME propellant then was charged into the aerosol can by methods well known in the art.

TABLES 1 and 2 summarize the compositions of Example 1–30 and list composition viscosity and spray pattern. The spray pattern of the aerosol compositions was evaluated visually as the spray leaves the can and falls onto the hair. A standard spray can with an actuator button having orifice diameter of 0.018 inch was used. The hair spray composition was sprayed in the air for about 10 seconds. A very bad or a bad spray pattern occurs when the composition sputters when leaving the actuator, the spray particles are too large or coarse (i.e., particle average diameter greater than 200 microns), the composition foams or clogs the actuator, or the spray cross section is narrow (i.e., less than 2 inches diameter). A marginal spray pattern is somewhat coarse, having an average particle diameter between 100 to 150 microns. A good spray pattern is a spray that leaves the can smoothly without sputtering or clogging, the spray particle size is fine, the particle average diameter is less than 100 microns, and there is no foaming. A spray from a standard pump bottle is evaluated in the same manner.

TABLE 1

Hair Spray Compositions Containing a Low Molecular Weight Carboxylated Polyurethane and a Second Hair Fixative Resin

| Example No. | Polyurethane Resin $B^1$ (% wt) | Second Hair Fixative Resin[2] (% wt) | VOC (% wt) | Water (% wt) | Resin Ratio[3] | Viscosity (cs) | Spray Pattern |
|---|---|---|---|---|---|---|---|
| 1 | 2.00 | 1.00 | 55.0 | 42.0 | 0.50 | 6.74 | good |
| 2 | 2.00 | 1.00 | 80.0 | 17.0 | 0.50 | 4.58 | good |
| 3 | 4.00 | 2.00 | 55.0 | 39.0 | 0.50 | 11.88 | good |
| 4 | 4.00 | 2.00 | 80.0 | 14.0 | 0.50 | 7.22 | good |
| 5 | 1.00 | 2.00 | 55.0 | 42.0 | 2.00 | 8.45 | good |
| 6 | 1.00 | 2.00 | 80.0 | 17.0 | 2.00 | 5.34 | good |
| 7 | 2.00 | 4.00 | 55.0 | 39.0 | 2.00 | 12.59 | good |
| 8 | 2.00 | 4.00 | 80.0 | 14.0 | 2.00 | 8.19 | good |
| 9 | 2.25 | 2.25 | 55.0 | 40.5 | 1.00 | 9.81 | good |
| 10 | 2.25 | 2.25 | 80.0 | 15.5 | 1.00 | 5.79 | good |
| 11 | 1.50 | 1.50 | 67.5 | 29.5 | 1.00 | 5.56 | good |
| 12 | 3.00 | 3.00 | 67.5 | 26.5 | 1.00 | 9.61 | good |
| 13 | 3.00 | 1.50 | 67.5 | 28.0 | 0.50 | 6.64 | good |

TABLE 1-continued

Hair Spray Compositions Containing a Low Molecular Weight Carboxylated Polyurethane and a Second Hair Fixative Resin

| Example No. | Polyurethane Resin B[1] (% wt) | Second Hair Fixative Resin[2] (% wt) | VOC (% wt) | Water (% wt) | Resin Ratio[3] | Viscosity (cs) | Spray Pattern |
|---|---|---|---|---|---|---|---|
| 14 | 1.50 | 3.00 | 67.5 | 28.0 | 2.00 | 7.83 | good |
| 15 | 2.25 | 2.25 | 67.5 | 28.0 | 1.00 | 7.68 | good |

[1]A carboxylated polyurethane resin having a weight average molecular weight of about 15,000 and an R-value of 0.65, prepared according to the method described in Example B;
[2]GANTREZ® A425, a partial butyl ester of a copolymer of vinyl methyl ether and maleic anhydride, available commercially from ISP, Wayne, NJ; and
[3]Ratio of second hair fixative resin to polyurethane resin.

TABLE 2

Hair Spray Compositions Containing a High Molecular Weight Carboxylated Polyurethane and a Second Hair Fixative Resin

| Example No. | Polyurethane Resin C[4] (% wt) | Second Hair Fixative Resin[2] (% wt) | VOC (% wt) | Water (% wt) | Resin Ratio[3] | Viscosity (cs) | Spray Pattern |
|---|---|---|---|---|---|---|---|
| 16 | 2.00 | 1.00 | 55.0 | 42.0 | 0.5 | 6.57 | foams, bad |
| 17 | 2.00 | 1.00 | 80.0 | 17.0 | 0.5 | 5.08 | good |
| 18 | 4.00 | 2.00 | 55.0 | 39.0 | 0.5 | 21.50 | foams, bad |
| 19 | 4.00 | 2.00 | 80.0 | 14.0 | 0.5 | 13.00 | foams, bad |
| 20 | 1.00 | 2.00 | 55.0 | 42.0 | 2.0 | 9.88 | good |
| 21 | 1.00 | 2.00 | 80.0 | 17.0 | 2.0 | 6.09 | good |
| 22 | 2.00 | 4.00 | 55.0 | 39.0 | 2.0 | 19.19 | foams, bad |
| 23 | 2.00 | 4.00 | 80.0 | 14.0 | 2.0 | 11.52 | good |
| 24 | 2.25 | 2.25 | 55.0 | 40.5 | 1.0 | 15.01 | foams, bad |
| 25 | 2.25 | 2.25 | 80.0 | 15.5 | 1.0 | 9.23 | good |
| 26 | 1.50 | 1.50 | 67.5 | 29.5 | 1.0 | 8.72 | good |
| 27 | 3.00 | 3.00 | 67.5 | 26.5 | 1.0 | 12.26 | bad, foams |
| 28 | 3.00 | 1.50 | 67.5 | 28.0 | 0.5 | 12.30 | bad, foams |
| 29 | 1.50 | 3.00 | 67.5 | 28.0 | 2.0 | 11.38 | bad, foams |
| 30 | 2.25 | 2.25 | 67.5 | 28.0 | 1.0 | 16.71 | bad, foams |

[4]A carboxylated polyurethane resin having a weight average molecular weight of about 40,000 and an R-value of about 0.85, prepared according to the method described in Example C.

Examples 1–30 in TABLES 1 and 2 show that aerosol hair spray compositions containing a carboxylated polyurethane resin and a conventional, second hair fixative resin, and having a low VOC (i.e., 55% by weight) and a low viscosity, can be prepared. The second hair fixative resin is sufficiently solubilized, or dispersed, in the water-ethanol solvent, and the hair spray composition has a sufficiently low viscosity for effective application to the hair. For example, Example 7 containing 4.00% by weight of the second hair fixative resin in a 55% VOC composition, had a viscosity of 12.59 cs and a good spray pattern.

Table 1 further shows a low composition viscosity and a good spray pattern for hair spray compositions containing a low molecular weight carboxylated polyurethane resin (e.g., $M_w$ about 15,000), even when the resin ratio of second hair fixative resin to polyurethane resin is greater than one, over the entire VOC range of 55% to 80% by weight. With respect to the high molecular weight polyurethane resin used in Examples 16–30 (e.g., $M_w$ about 40,000), a good spray pattern can be obtained for 80% by weight VOC compositions (e.g., see Example 17), and for 55% by weight VOC compositions when the total amount of resin (i.e., sum of the polyurethane resin and second hair fixative resin) is relatively low, i.e., about 0.5% to about 3% by weight of the composition.

As previously described, the carboxylated polyurethane resins are copolymers containing hydrophobic blocks and hydrophilic blocks. It is theorized, but not relied upon herein, that the hydrophobic blocks have a tendency to associate with one another in aqueous solution and generate physical crosslinks which have the effect of increasing the viscosity of the solution. The data in TABLE 3 illustrates that the viscosity of carboxylated polyurethane solutions increases as the ratio of water to ethanol in the solution increases. This viscosity increase is attributed to the associative nature of the hydrophobic blocks of the polyurethane resin, i.e., as the water content of the solution increases, the hydrophobic blocks of the resin associate to achieve thermodynamic equilibrium. This associative behavior produces physical crosslinks which increase viscosity and ultimately leads to gelation. This associative effect is more pronounced when a high molecular weight polyurethane resin is dissolved, i.e., compare Polyurethane Resin B ($M_w$ 15,000) to Polyurethane Resin A ($M_w$ 76,000).

Accordingly, a present hair spray composition contains a carboxylated polyurethane resin having a weight average molecular weight of about 10,000 to about 75,000. At a molecular weight below about 10,000, the carboxylated polyurethane resin cannot hold the hair in a predetermined configuration for a sufficient time to meet consumer demands. If the molecular weight is greater than about 75,000, composition viscosity can be too high for effective application to the hair, especially at a low VOC and a high concentration of carboxylated polyurethane resin and second hair fixative resin.

TABLE 3

| Polyurethane Resin (5% wt/wt) | Ethanol (wt %) | Viscosity at 25° C. (cs) | Measuring System | Solution Appearance |
|---|---|---|---|---|
| Resin B[1] | 80 | | | clear |
| Resin B[1] | 55 | 7.05 | capillary viscometer | slightly hazy |
| Resin B[1] | 35 | 9.34 | capillary viscometer | hazy |
| Resin B[1] | 25 | 13.08 | capillary viscometer | hazy |
| Resin B[1] | 10 | 19.83 | capillary viscometer | slightly hazy |
| Resin C[4] | 80 | | | clear |
| Resin C[4] | 55 | 13.15 | capillary viscometer | slightly hazy |
| Resin C[4] | 35 | 80 cp | Brookfield, #4 spindle 10 rpm | clear |
| Resin C[4] | 25 | 5,600 | Brookfield, #4 spindle, 10 rpm | clear |
| Resin C[4] | 10 | 40,000 | Brookfield, #7 spindle, 10 rpm | clear |
| Resin A[5] | 80 | | | |
| Resin A[5] | 55 | 20.74 | capillary viscometer | |
| Resin A[5] | 35 | 2,400 | Brookfield, #4 spindle, 10 rpm | slightly hazy |
| Resin A[5] | 25 | 180,000 | Brookfield, #4 spindle 10 rpm | slightly hazy |
| Resin A[5] | 10 | stiff gel | | hazy, translucent |

[5]A carboxylated polyurethane resin having a weight average molecular weight of about 76,000 and an R-value of 0.85, prepared according to the method described in Example A.

Experiments also were performed which duplicate air drying of a hair spray composition after application to hair, i.e., drying without the assistance of heat, such as with a blow dryer. In general, the most volatile component of the composition, e.g., ethanol, evaporates the fastest, thereby making the composition richer in water. The data presented in TABLE 4 shows that as the ethanol evaporates, a carboxylated polyurethane (Example 31) and a composition of the present invention (Example 32) gel within one hour after application to the hair. In contrast, a composition containing only AMPHOMER, i.e., a second hair fixative resin (Example 33), did not gel after two hours.

The composition of Examples 31–33 were prepared by dissolving 3 parts by weight resin (total) in 55 parts by weight ethanol and 42 parts by weight water. Ten grams of each composition individually were placed in a glass Petri dish, and the composition was allowed to dry in open air at room temperature.

TABLE 4

| Example | Resin | 0 min. | 30 min. | 60 min. | 120 min. |
|---|---|---|---|---|---|
| 31 | Polyurethane Resin C[4] | liquid | viscous liquid | gel | gel |
| 32 | Blend of Polyurethane Resin C[4] and AMPHOMER[7] | liquid | viscous liquid | gel | gel |
| 33 | AMPHOMER[6] | liquid | liquid | liquid | viscous liquid |

[6]AMPHOMER is a commercial hair fixative resin available from National Starch and Chemical Corp., Bridgewater, NJ and is an octylacrylamide/acrylates/butylaminoethyl methacrylate copolymer; and
[7]The weight ratio of polyurethane resin to AMPHOMER was 1:1, and the AMPHOMER was 100% neutralized with 2-amino-2-methyl-propane (AMP).

TABLE 4 shows that Example 32, a composition of the present invention, is a liquid composition that is capable of gelling after application to hair. A hair setting composition containing only AMPHOMER does not gel, or gels after an extended time.

Figure 1:
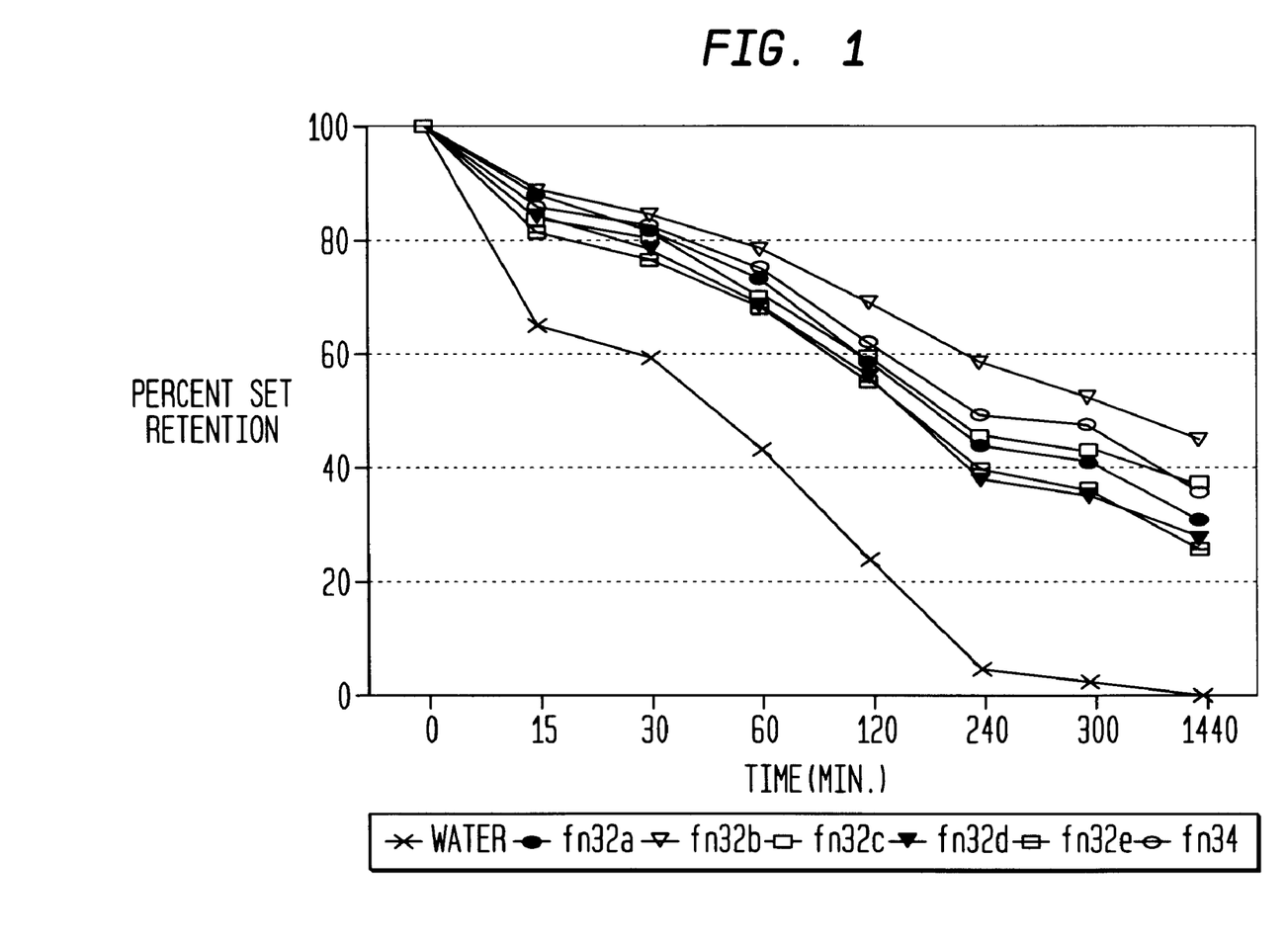
FIG. 1 is a plot of percent set retention vs. time (minutes) comparing the ability of hair spray compositions to retain a hair set at 85% relative humidity and 25° C.

Other experiments were performed to illustrate the advantages of a hair spray composition containing a blend of a carboxylated polyurethane resin and a second hair fixative resin. In particular, the hair spray compositions were tested for an ability to maintain a hair set. FIG. 1 is a plot of percent set retention vs. time for hair treated with various hair setting compositions. The hair setting compositions were compared to water as a negative control. The following six hair setting compositions were prepared:

fn32a—3% Polyurethane Resin B (comparative)

fn32b—3% AMPHOMER, 100% neutralized with AMP (comparative)

fn32c—3% GANTREZ A425, 20% neutralized with AMP (comparative)

fn32d—2% Polyurethane Resin B and 1% AMPHOMER (100% neutralized with AMP)

fn32e—2% Polyurethane Resin B and 1% GANTREZ (20% neutralized)

fn34a—0.5% Polyurethane Resin C and 1% AMPHOMER (100% neutralized with AMP)

The above compositions were prepared by dissolving the resins in a 55/42 ethanol-to-water solution.

Set retention test measures the ability of a hair spray composition to hold or retain a hair style for an extended time at a particular relative humidity. Set retention was measured by applying 0.5 cc (cubic centimeter) of the hair spray composition to a one gram hair tress, and testing six or more tresses per composition. The sprayed tresses were allowed to dry overnight, at 30% relative humidity (i.e., RH), in a zigzag shape. The tresses were hung inside a humidity chamber at 25° C. and a predetermined relative humidity (i.e., 85% RH). The relaxed length was recorded of the tresses and set retention was calculated using the equation:

$$\% \text{ Set Retention} = \frac{L - L_t}{L - L_o} \times 100,$$

wherein L is the length of the fully extended tress, $L_o$ is the length of sprayed hair before relaxation, $L_t$ is the length after exposure for a time, t. Six or more tresses were tested per hair spray composition and the data was statistically analyzed and compared at the 95% confidence level.

FIG. 1 summarizes the hair set retention tests. The hair set retention results were compared to the results provided by a negative control containing only water. The comparative test shows that hair spray compositions containing a carboxylated polyurethane and a second hair fixative resin performed essentially as well as a hair spray composition containing only AMPHOMER. Such results are good because AMPHOMER is the hair fixative resin used in successful commercial hair spray compositions.

A hair spray composition must also possess properties in addition to set retention in order to meet consumer demands. In particular, useful hair spray compositions impart a soft, natural, and nontacky feel to the hair and avoid excessive flaking and crust. TABLE 5 summarizes the results of tests on hair spray compositions containing 3 to 5% by weight of a low molecular weight polyurethane resin, 0 to 1% by weight GANTREZ A425 as the second hair fixative resin, and 55% ethanol. The resulting compositions, i.e., Examples 34–41, were tested for average crust, average feel, and average flaking.

The hair crust test measures the hardness and/or stiffness of hair sprayed with a hair spray composition. Hair spray compositions that provide natural, or reduced, crusts are desired. Hair crust was tested subjectively by a group of trained judges. The judges evaluated hair tresses sprayed with a present hair spray composition containing a polyurethane resin and a second hair fixative resin, or with the control composition. The hair flaking test measures the amount of flakes or dust that form on the hair after combing hair that has been sprayed with the composition and dried.

TABLE 5

| | Example | | | | | | | |
|---|---|---|---|---|---|---|---|---|
| | 34 | 35 | 36 | 37 | 38 | 39 | 40 | 41 |
| | | | | % wt/wt | | | | |
| Ingredient | | | | | | | | |
| Ethanol | 55.00 | 55.00 | 55.00 | 55.00 | 55.00 | 55.00 | 55.00 | 55.00 |
| Polyurethane Resin B[1] | 3.00 | 3.00 | 3.00 | 5.00 | 4.00 | 4.00 | 5.00 | 5.00 |
| GANTREZ A425 | 0 | 0.50 | 1.00 | 0 | 0.50 | 1.00 | 0.50 | 1.00 |
| AMP | 0 | 0.09 | 0.18 | 0 | 0.09 | 0.18 | 0.09 | 0.18 |
| D.I. Water | 42 | 41.41 | 40.82 | 40 | 40.41 | 39.82 | 39.41 | 38.82 |
| Total | 100.00 | 100.00 | 100.00 | 100.00 | 100.00 | 100.00 | 100.00 | 100.00 |
| Performance | | | | | | | | |
| Avg. Crust[8] | 4.75 | 3.50 | 4.23 | n/a | 7.00 | 8.30 | 9.10 | 9.43 |
| Avg. Feel[9] | 4.00 | 2.60 | 3.33 | 9.00 | 5.50 | 5.66 | 7.50 | 8.66 |
| Avg. Flaking[10] | 7.00 | 3.33 | 4.5 | 9.00 | 6.80 | 6.33 | 7.66 | 8.83 |

[8]Average crust was evaluated by two to five judges compressing a treated hair curl between the fingers, and rated on a scale of 1 to 9, wherein 1 = natural hair and 10 = very crusty;
[9]Average feel was evaluated by two to five judges, for degree of raspiness, coating and gluing effect of treated hair tresses, and rated on a scale of 1 to 9, wherein 1 = natural hair and 10 = very raspy, coated, and/or glued hair; and
[10]Average flaking was evaluated by two to five judges, wherein treated, dried hair tresses were combed and visually rated for amount of flaking.

The data summarized in TABLE 5 demonstrates that blending a low molecular weight carboxylated polyurethane with a second hair fixative resin (i.e., GANTREZ A425) results in an improvement of the overall properties of the hair spray compositions.

TABLE 6 contains data for low VOC hair spray compositions containing a low molecular weight carboxylated polyurethane resin and a second hair fixative resin. Examples 42–49 in TABLE 6 demonstrate that blending a low molecular weight polyurethane with AMPHOMER results in improved overall properties of the hair spray compositions.

TABLE 6

| | Example | | | | | | | |
|---|---|---|---|---|---|---|---|---|
| | 42 | 43 | 44 | 45 | 46 | 47 | 48 | 49 |
| | | | | % wt/wt | | | | |
| Ingredient | | | | | | | | |
| Ethanol | 55.00 | 55.00 | 55.00 | 55.00 | 55.00 | 55.00 | 55.00 | 55.00 |
| Polyurethane Resin B[1] | 3.00 | 3.00 | 3.00 | 5.00 | 4.00 | 4.00 | 5.00 | 5.00 |
| AMPHOMER[6] | 0 | 0.50 | 1.00 | 0 | 0.50 | 1.00 | 0.50 | 1.00 |
| AMP | 0 | 0.09 | 0.18 | 0 | 0.09 | 0.18 | 0.09 | 0.18 |
| D.I. Water | 42.00 | 41.41 | 40.82 | 40.00 | 40.41 | 39.82 | 39.41 | 38.82 |
| Total | 100.00 | 100.00 | 100.00 | 100.00 | 100.00 | 100.00 | 100.00 | 100.00 |
| Performance | | | | | | | | |
| Avg. Crust[8] | 4.75 | 3.00 | 3.75 | n/a | 6.38 | 6.75 | 7.00 | 9.00 |
| Avg. Feel[9] | 4.0 | 4.25 | 4.88 | 9.0 | 7.10 | 7.50 | 8.50 | 8.75 |
| Avg. Flaking[10] | 7.0 | 2.92 | 3.25 | 9.0 | 6.00 | 6.50 | 7.86 | 8.75 |

In other tests, a high molecular weight carboxylated polyurethane was blended with a second hair fixative resin and the resulting hair spray compositions were tested for crust, feel, and flaking after application to the hair. The compositions and test results are set forth in Examples 50–56 in TABLE 7 and Examples 57–63 in TABLE 8.

Examples 50–56 show that a blend of a relatively high molecular weight polyurethane resin with GANTREZ A425 results in an overall improvement in the properties of the hair spray composition. Examples 50–56 also show that a blend of resins allows a formulator the opportunity to design a hair spray composition having specific properties, such as natural hair feel or a stiff hair feel, by simply choosing a proper ratio of carboxylated polyurethane resin. to second hair fixative resin. Comparing TABLES 5 and 7 shows that good performance properties are obtained using a relatively low concentration of a high molecular weight polyurethane resin in the hair spray composition.

Examples 57–63 in TABLE 8 are similar to the compositions summarized in TABLE 7, except the second hair fixative resin in Examples 57–63 was AMPHOMER. The results summarized in TABLES 7 and 8 are similar.

TABLE 7

| | Example | | | | | | |
|---|---|---|---|---|---|---|---|
| | 50 | 51 | 52 | 53 | 54 | 55 | 56 |
| | | | | % wt/wt | | | |
| Ingredient | | | | | | | |
| Ethanol | 55.00 | 55.00 | 55.00 | 55.00 | 55.00 | 55.00 | 55.00 |
| Polyurethane Resin B[1] | 1.00 | 0.50 | 0.05 | 0.75 | 0.75 | 1.00 | 1.00 |
| GANTREZ A425 | 0 | 0.50 | 1.00 | 0.50 | 1.00 | 0.50 | 1.00 |
| AMP | 0 | 0.09 | 0.18 | 0.09 | 0.18 | 0.09 | 0.18 |
| D.I. Water | 44.00 | 43.91 | 43.77 | 43.66 | 43.07 | 43.41 | 42.82 |
| Total | 100.00 | 100.00 | 100.00 | 100.00 | 100.00 | 100.00 | 100.00 |
| Performance | | | | | | | | 
| Avg. Crust[8] | 5.00 | 2.75 | 7.3 | 5.15 | 8.65 | 6.35 | 9.25 |
| Avg. Feel[9] | 4.75 | 1.25 | 4.25 | 3.75 | 6.85 | 5.65 | 7.75 |
| Avg. Flaking[10] | 7.00 | 3.15 | 4.25 | 3.85 | 8.25 | 7.65 | 7.05 |

TABLE 8

| | Example | | | | | | |
|---|---|---|---|---|---|---|---|
| | 57 | 58 | 59 | 60 | 61 | 62 | 63 |
| | | | | % wt/wt | | | |
| Ingredient | | | | | | | |
| Ethanol | 55.00 | 55.00 | 55.00 | 55.00 | 55.00 | 55.00 | 55.00 |
| Polyurethane Resin B[1] | 1.00 | 0.50 | 0.50 | 0.75 | 0.75 | 1.00 | 1.00 |
| AMPHOMER[6] | 0 | 0.50 | 1.00 | 0.50 | 1.00 | 0.50 | 1.00 |
| AMP | 0 | 0.09 | 0.18 | 0.09 | 0.18 | 0.09 | 0.18 |
| D.I. Water | 44.00 | 43.91 | 43.77 | 43.66 | 43.07 | 43.41 | 42.82 |
| Total | 100.00 | 100.00 | 100.00 | 100.00 | 100.00 | 100.00 | 100.00 |

TABLE 8-continued

| | Example | | | | | | |
|---|---|---|---|---|---|---|---|
| | 57 | 58 | 59 | 60 | 61 | 62 | 63 |
| | | | | % wt/wt | | | |
| Performance | | | | | | | |
| Avg. Crust[8] | 5.00 | 4.00 | 5.00 | 5.50 | 6.50 | 5.50 | 7.00 |
| Avg. Feel[9] | 4.75 | 4.50 | 4.50 | 6.00 | 5.50 | 7.50 | 8.00 |
| Avg. Flaking[10] | 7.00 | 1.00 | 1.50 | 1.75 | 2.25 | 4.00 | 5.00 |

Another important property of a present hair spray composition is the ability to wash the hair setting resins from the hair, and thereby avoid polymer build-up on the hair. In accordance with an important feature of the present invention, the carboxylated polyurethane resin and the second hair fixative resin used in the hair spray composition can be removed from the hair by simply shampooing the hair. The unexpected washability of the hair spray composition is attributed to the hydrophilic nature of the polyurethane resin, and especially to the acid value of the carboxylated polyurethane resin. When the acid value of the carboxylated polyurethane resin is at least 7 mg KOH/g of resin, e.g., about 7 to about 50 mg KOH/g resin, the polyurethane resin can be rinsed from the hair during shampooing without the need to neutralize the resin with an organic base.

The acid value is an indication of the number pendant carboxylic acid groups on the polyurethane resin backbone. Although noncarboxylated polyurethane resins are hydrophilic, they are difficult to wash from the hair in a short time. Washability is enhanced by incorporating pendant carboxylic acid groups onto the polyurethane backbone.

The effect of acid value is illustrated by Polyurethane Resins B and C, which show that washability is independent of $M_w$ or R-value, but requires a carboxylated polyurethane resin having an acid value of 7 mg KOH/g of resin or greater, e.g., about 7 to about 50 mg KOH/g resin. In particular, Polyurethane Resin B has an R-value of 0.65, a molecular weight of about 15,000, and an acid value of 24.22. Polyurethane Resin C has an R-value of 0.85, a molecular weight of about 40,000, and an acid value of 8.01. Polyurethane Resins B and C each are washable from hair because each has an acid value of at least 7 mg KOH/g of resin.

The acid value was measured by titrating a solution of the resin with potassium hydroxide. The acid value is expressed in milligrams of KOH per gram of carboxylated polyurethane resin. The washability of the resin was determined by applying 3 wt. % solution of polyurethane resin onto clean, 2 gram, 6-inch long hair tresses, allowing the hair to dry, then washing the hair tresses with shampoo and warm water for about 3 minutes.

Many modifications and variations of the invention as hereinbefore set forth can be made without department from the spirit and scope thereof, and, therefore, only such limitations should be imposed as are indicated by the appended claims.

What is claimed is:

1. A hair spray composition consisting of
   (a) about 0.25% to about 6% by weight of a carboxylated polyurethane resin;
   (b) 0% to about 6% by weight of a second hair fixative resin;
   (c) 0% to about 80% by weight of an alcohol;
   (d) about 15% to about 95% by weight water;
   wherein the carboxylated polyurethane resin has a weight average molecular weight of about 10,000 to about 80,000, a polydispersibility index of about 1 to about 4, an acid value of about 7 mg to about 50 mg KOH/g of resin, a melting point of about 40° C. to about 100° C., and is a reaction product of a mixture consisting essentially of:
   (i) about 10% to about 90% by weight of the mixture of a polyoxyalkylene diol having a number average molecular weight of about 200 to about 10,000
   (ii) about 0.01 % to about 20% by weight of the mixture of an alkylene glycol;
   (iii) about 3% to about 80% by weight of the mixture of an organic diisocyanate;
   (iv) about 10% to about 8% by weight of the mixture of a 2,2-di(hydroxymethyl)alkanoic acid; and
   (v) about 0.1% to about 0.5% by weight of the mixture of water, wherein a ratio of isocyanate groups to hydroxyl groups is about 0.5 to about 9.0.

* * * * *